US007654463B2

(12) United States Patent
Mitamura

(10) Patent No.: US 7,654,463 B2
(45) Date of Patent: Feb. 2, 2010

(54) ELECTRONIC DOCUMENT MANAGEMENT SYSTEM, MEDICAL INFORMATION SYSTEM, METHOD FOR PRINTING SHEET OF CHART PAPER, AND SHEET OF CHART PAPER

(75) Inventor: Yoshihiko Mitamura, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 11/444,471

(22) Filed: Jun. 1, 2006

(65) Prior Publication Data

US 2007/0090177 A1    Apr. 26, 2007

(30) Foreign Application Priority Data

Oct. 24, 2005    (JP)    ............................. 2005-308904

(51) Int. Cl.
*G06K 7/10*    (2006.01)
(52) U.S. Cl. .................... 235/472.03; 235/468; 235/494
(58) Field of Classification Search ................ 235/454, 235/472.03, 491, 494
See application file for complete search history.

(56) References Cited

U.S. PATENT DOCUMENTS

| | | | | |
|---|---|---|---|---|
| 6,689,966 | B2* | 2/2004 | Wiebe ...................... | 178/18.01 |
| 6,854,821 | B2* | 2/2005 | Ericson et al. ................. | 347/14 |
| 6,864,880 | B2* | 3/2005 | Hugosson et al. ........... | 345/162 |
| 7,072,529 | B2* | 7/2006 | Hugosson et al. ........... | 382/305 |
| 7,082,444 | B2* | 7/2006 | Braun et al. ................. | 707/203 |
| 2002/0011989 | A1* | 1/2002 | Ericson et al. ............... | 345/158 |
| 2003/0053699 | A1* | 3/2003 | Olsson ........................ | 382/228 |
| 2003/0117652 | A1* | 6/2003 | Lapstun ..................... | 358/1.18 |
| 2004/0000585 | A1* | 1/2004 | Silverbrook et al. ......... | 235/383 |
| 2004/0064787 | A1* | 4/2004 | Braun et al. ................. | 715/505 |
| 2004/0083138 | A1* | 4/2004 | Silverbrook et al. .......... | 705/26 |
| 2004/0190085 | A1* | 9/2004 | Silverbrook et al. ........ | 358/474 |
| 2004/0190092 | A1* | 9/2004 | Silverbrook et al. ........ | 358/539 |
| 2004/0195342 | A1* | 10/2004 | Silverbrook et al. ........ | 235/494 |
| 2004/0196501 | A1* | 10/2004 | Silverbrook et al. ....... | 358/1.15 |
| 2005/0060644 | A1* | 3/2005 | Patterson .................... | 715/505 |

(Continued)

FOREIGN PATENT DOCUMENTS

JP    A-2003-203121    7/2003

(Continued)

OTHER PUBLICATIONS

U.S. Appl. No. 11/250,401, filed Oct. 17, 2005 in the name of Takeshi Onishi et al.

(Continued)

*Primary Examiner*—Daniel A Hess
*Assistant Examiner*—Paultep Savusdiphol
(74) *Attorney, Agent, or Firm*—Oliff & Berridge, PLC

(57) ABSTRACT

An electronic document management system includes an acquisition unit, a specifying unit and a database. A medium includes a document image and a plurality of code image two-dimensionally arranged. Each code image includes position information and medium identification information. The acquisition unit acquires a code image corresponding to an operation position on the medium in conjunction with a user's operation with respect to the medium. The specifying unit specifies the medium identification information included in the code image acquired by the acquisition unit. The database stores personal information associated with the medium identification information specified by the specifying unit.

19 Claims, 8 Drawing Sheets

U.S. PATENT DOCUMENTS

| | | | |
|---|---|---|---|
| 2005/0099409 A1* | 5/2005 | Brouhon | 345/179 |
| 2005/0243369 A1* | 11/2005 | Goldstein et al. | 358/1.18 |
| 2006/0033725 A1* | 2/2006 | Marggraff et al. | 345/179 |
| 2006/0047539 A1* | 3/2006 | Huang | 705/4 |
| 2006/0085222 A1* | 4/2006 | Huang et al. | 705/2 |
| 2007/0008304 A1* | 1/2007 | Tobin | 345/179 |

FOREIGN PATENT DOCUMENTS

| | | |
|---|---|---|
| JP | A-2004-102972 | 4/2004 |

OTHER PUBLICATIONS

U.S. Appl. No. 11/372,197, filed Mar. 10, 2006 in the name of Takeshi Onishi.

* cited by examiner

FIG. 5

2005.02/03 AM10:38:42 INTERNAL MEDICINE ID0012

MEDICAL RECORD

- PATIENT NAME: TARO FUJI
- PATIENT ID: PATIENT ID-0024048
- DATE OF BIRTH: 1068.10.31
- MEDICAL CLASSIFICATION: REEXAMINATION
- TIME AND DATE OF HOSPITAL VISIT: 2005.02.03 AM10.35
- MEDICAL DEPARTMENT: NEURAL INTERNAL MEDICINE
- ATTENDING DOCTOR: KUSURO REI
- PREVIOUS HOSPITAL VISIT
- ANAMNESIS: NONE
- ALLERGY: NONE
- PREVIOUS HOSPITAL VISIT: 2005.01.25

~~FUJI CENTRAL~~

| ENTRY FIELD (ENTRY BY ELECTRONIC PEN) | FUNCTION SELECTION FIELD |
|---|---|
| 2005/2/3<br>backack, since a half year ago, when do housework.<br>These days, can't sleep due to pain.<br><br>backack → roentgen → no abnormality<br>blood test<br>  hemoglobin 7.8 g/dl ) normocytic anemia<br>  MCV 101 fl<br>  total protein 8.6 g/dl<br>  LDH 286 IV/l<br>  Creatinine 2.0 mg/dl<br>  Serum Ca²⁺ 12.6 mg/dl    hypocalcemia<br>  immune serum IgA 4000mg/dl<br>                               dehydration<br>(hospitalization)<br><br>2005/2/4<br>  intravenous injection<br>  further testing: urine Bence-Jones protein + M protein IgGk<br>  CR: skull<br>  marrow: plasma 20%<br>                    myeloma multiplex | S ☑☑☐☐<br><br>O ☑☑☐☐<br><br>A ☑☐☐☐<br><br>P ☑☐☐☐<br><br>PAST HISTORY<br>View ☑☐☐☐<br><br>INSPECTION<br>IN ☑☑☐☐<br>View ☑☐☐☐<br><br>TREATMENT<br>IN ☐☐☐☐<br>View ☐☐☐☐<br><br>PRESCRIPTION<br>IN ☑☐☐☐<br>View ☑☐☐☐<br><br>RESERVATION<br>IN ☑☐☐☐<br>View ☐☐☐☐ |

FUJI CENTRAL HOSPITAL, INTERNAL MEDICINE

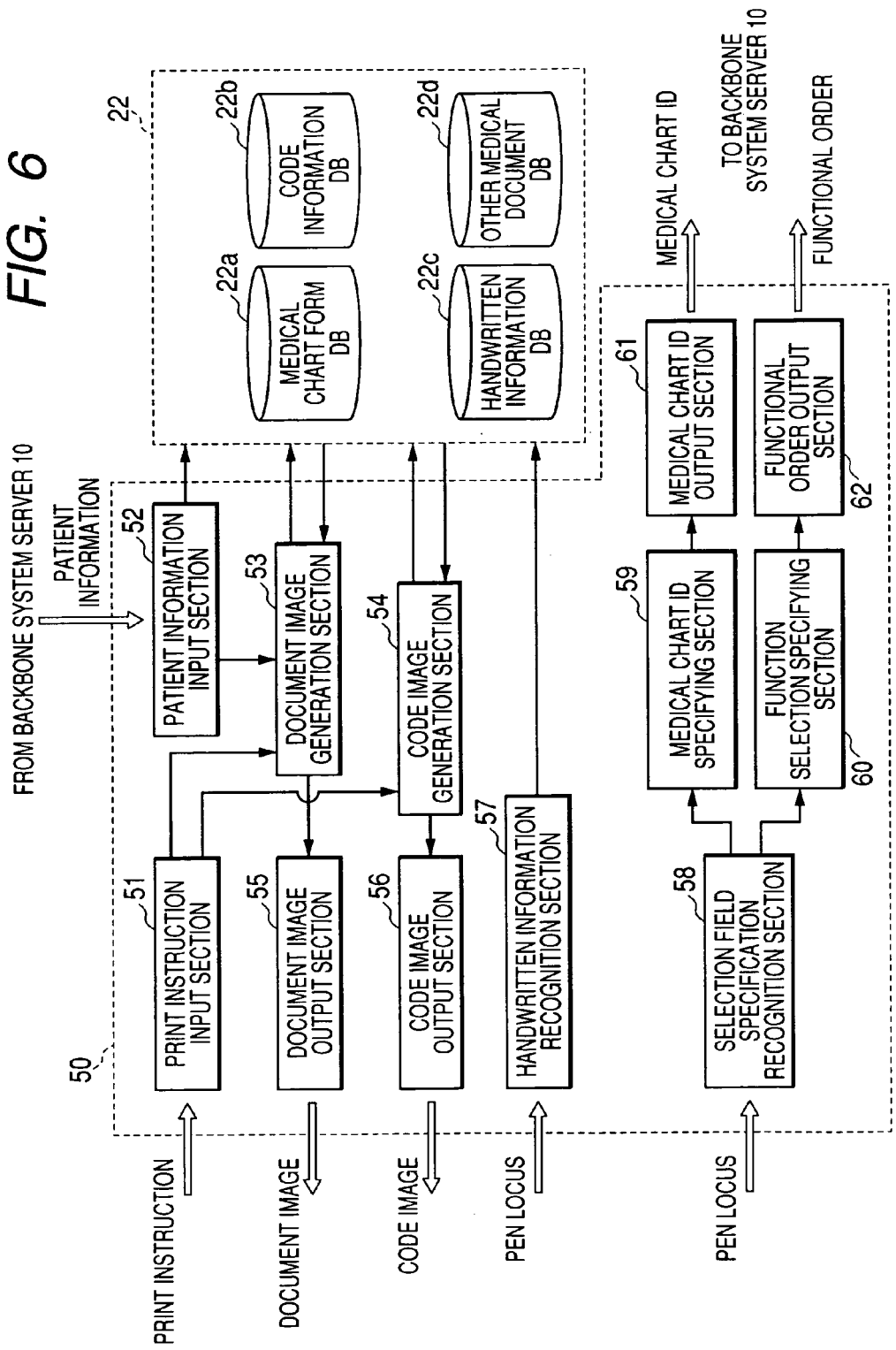

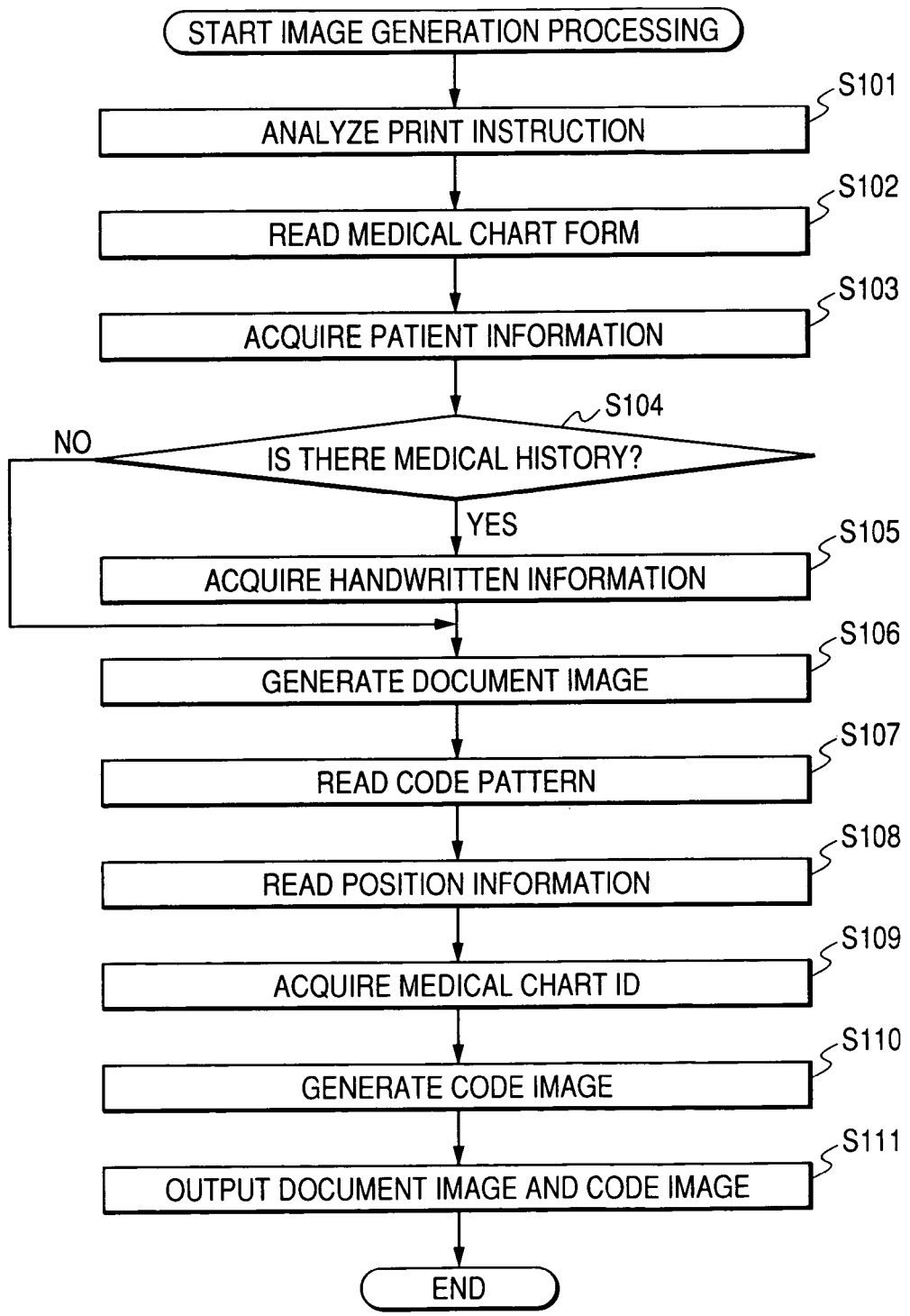

FIG. 8A

| MEDICAL CHART ID ~31 | PATIENT ID ~32 | S_Box_1 ~33 | ..... | INSPECTION BOX_1 ~34 | ..... | RESERVATION BOX_1 ~35 |
|---|---|---|---|---|---|---|
| A000000001 | P000000111 | S00020001 | ..... | K111000003 | ..... | Y110333499 |
| A000000002 | P000000112 | S00020002 | ..... | K111000004 | ..... | Y110333500 |
| A000000003 | P000000113 | S00020003 | ..... | K111000005 | ..... | Y110333501 |
| A000000004 | P000000114 | S00020004 | ..... | K111000006 | ..... | Y110333502 |
| A000000005 | P000000115 | S00020005 | ..... | K111000007 | ..... | Y110333503 |
| A000000006 | P000000116 | S00020006 | ..... | K111000008 | ..... | Y110333504 |
| A000000007 | P000000117 | S00020007 | ..... | K111000009 | ..... | Y110333505 |
| ..... | ..... | ..... | ..... | ..... | ..... | ..... |

FIG. 8B

| PATIENT ID ~36 | NAME | DATE OF BIRTH | LAST DAY OF HOSPITAL VISIT | ATTENDING DOCTOR | ..... | ALLERGY |
|---|---|---|---|---|---|---|
| P000000111 | TARO FUJI | S30.5.6 | H5.8.12 | ICHIRO SUZUKI | ..... | NONE |
| ..... | ..... | ..... | ..... | ..... | ..... | ..... |

FIG. 8C

| INSPECTION ID ~37 | INSPECTION TYPE | TIME AND DATE OF INSPECTION REQUEST | INSPECTION REQUEST Dr | TIME AND DATE OF INSPECTION | ..... | INSPECTION IMAGE ~38 |
|---|---|---|---|---|---|---|
| K111000003 | CHEST ROENTGEN | H5.8.12 | ICHIRO SUZUKI | H5.8.12 | ..... | KI350002134 |
| ..... | ..... | ..... | ..... | ..... | ..... | ..... |

ELECTRONIC DOCUMENT MANAGEMENT SYSTEM, MEDICAL INFORMATION SYSTEM, METHOD FOR PRINTING SHEET OF CHART PAPER, AND SHEET OF CHART PAPER

This application claims priority under 35 U.S.C. §119 from Japanese patent application No. 2005-308904 filed on Oct. 24, 2005, the disclosure of which is incorporated by reference herein.

BACKGROUND

1. Technical Field

The invention relates to a system for fusing paper and electronic information, and more particularly to a system capable of fusing paper and electronic information such as electronic medical information using a code image and a document image, which are formed on a medium.

2. Related Art

For the purpose of improvement in the quality of medical care and reduction in healthcare cost, in recent years, advances in IT (information technology) of a healthcare field have been made and various medical information systems have been proposed. The medical information systems mainly include (i) an electronic chart system, (ii) a remote medical support system, (iii) a receipt computer processing support system and (iv) an ordering system. However, particularly, most of the electronic chart systems intended for electronic storing, updating and sharing of medical records input the contents of a medical chart by means of a keyboard using a PC (personal computer). As a result, a doctor must concentrate on a PC screen during examination and an input operation of data may be an obstacle to the primary medical practice. Also, input information was limited to text information and simple graphic information. Input operability was not good. The amount of information described in a medical chart decreased.

SUMMARY

According to an aspect of the invention, an electronic document management system includes an acquisition unit, a specifying unit and a database. A medium includes a document image and a plurality of code images two-dimensionally arranged. Each code image includes position information and medium identification information. The acquisition unit acquires a code image corresponding to an operation position on the medium in conjunction with a user's operation with respect to the medium. The specifying unit specifies the medium identification information included in the code image acquired by the acquisition unit. The database stores personal information associated with the medium identification information specified by the specifying unit.

According to another aspect of the invention, a medical information system includes an electronic pen and a database. The electronic pen is used for a sheet of chart paper on which a plurality of code images are printed. Each code image is formed on a basis of medium identification information including information available to identify the medical chart. The electronic pen is used to write onto the sheet of chart paper. The electronic pen acquires a code image corresponding to an operation position on the sheet of chart paper in conjunction with a user's operation with respect to the sheet of chart paper. The database stores personal information while associating the personal information with the information available to identify the sheet of chart paper. It is made possible to access predetermined personal information stored in the database with using information available to identify the sheet of chart paper included in the code image acquired in conjunction with the user's operation of the electronic pen.

According to further another aspect of the invention, a method for printing a sheet of chart paper, includes: analyzing a print instruction; reading a chart form stored in a memory on a basis of the analyzed print instruction; acquiring patient information to be reflected on the sheet of chart paper; generating a document image on a basis of the patient information and the chart form; acquiring a chart ID while reading position information stored in the memory; generating a code image using the chart ID and the position information; and printing the generated document image and the code image onto a sheet of paper to print the sheet of chart paper.

According to still another aspect of the invention, a sheet of chart paper is used in medical practice. The sheet of chart paper is printed during the medical practice. The sheet of chart paper includes a document image and a code image. The document information includes a predetermined chart form and patient information. The document image is printed with a color material, which is recognizable with human eyes. The code image is printed on the sheet of chart paper with a color material having characteristic that a wavelength of a particular infrared region is absorbed more than a wavelength of a visible light region. Each code image includes position information that specifies a position on the sheet and identification information available to identify the sheet. The position information and the identification information are in a fine region, which can be readable by an electronic pen that captures a user's operation with respect to the sheet of chart paper.

BRIEF DESCRIPTION OF THE DRAWINGS

Embodiments of the invention will be described in detail based on the following figures, wherein:

FIG. 5 is a diagram showing an example of a medical chart form formed on the medical chart;

FIG. 6 is a block diagram showing one function of a medical document database and a paper information management server;

FIG. 7 is a flowchart showing image generation processing performed by the paper information management server shown in FIG. 6;

FIGS. 8A to 8C are diagrams showing data structures of a medical chart information database (DB), a patient information database (DB) and an inspection information database (DB) in a backbone DB.

DETAILED DESCRIPTION

An exemplary embodiment of the invention will be described below in detail with reference to the accompanying drawings.

Figure 1:
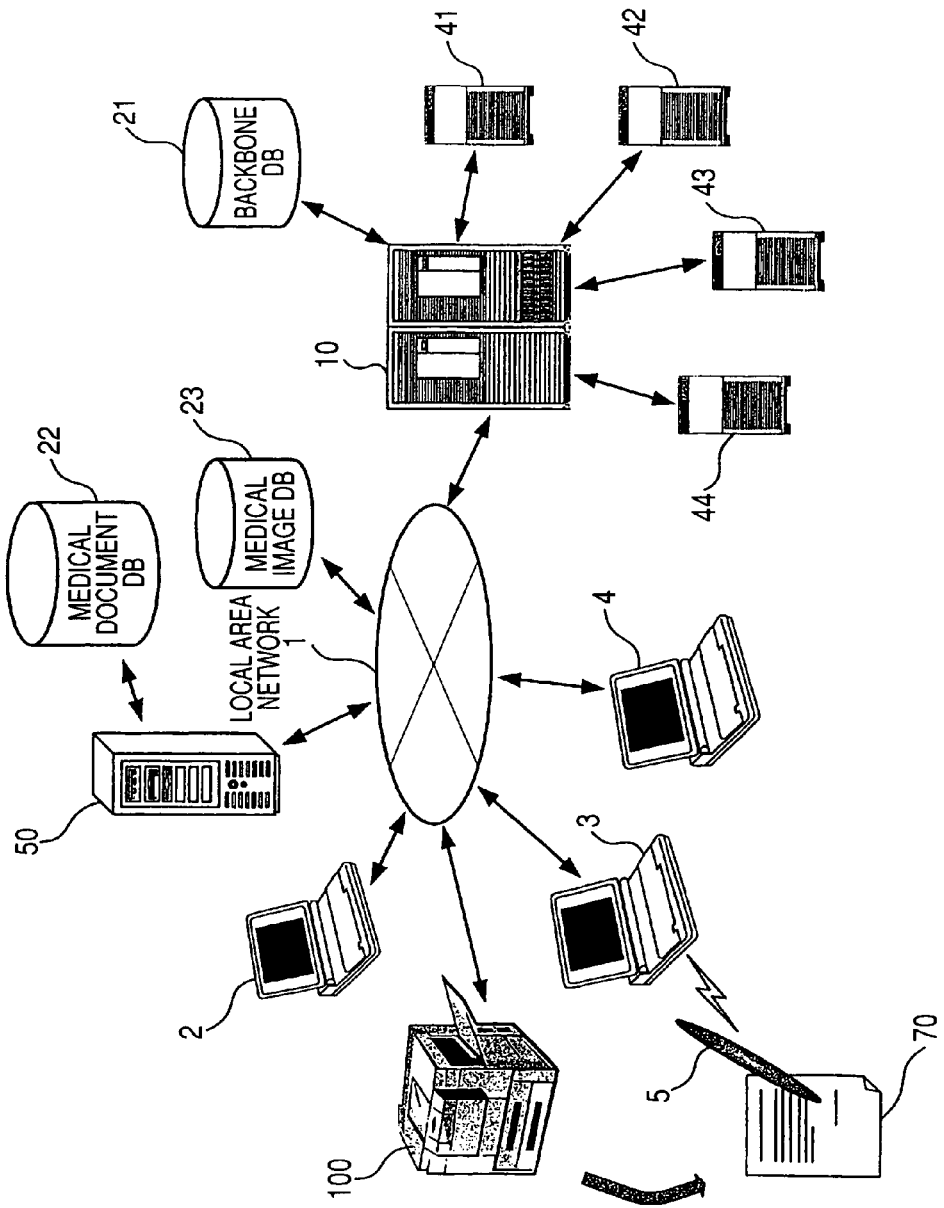
FIG. 1 shows one example of a configuration of a medical information system to which an exemplary embodiment is applied.

FIG. 1 shows one example of a configuration of a medical information system to which this exemplary embodiment is applied. This system functions as one electronic document management system, and various terminals, servers and computerizing systems are connected to a local area network 1 such as Ethernet (registered trademark) constructed inside a hospital. In this exemplary embodiment, an example of the medical information system will be described, but the electronic document management system can also be applied to an educational system or a merchandise management system.

In the medical information system shown in FIG. 1, a front desk terminal 2 through which various information is input at the front desk at the time when a patient visits a hospital and a doctor's terminal 3 used at the time when a doctor makes an examination are connected to the local area network 1. Also, various terminals 4 disposed in a cashier window, a medical coding center and a dispensing pharmacy are connected to the local area network 1. Also, as computerizing systems, for example, a backbone system server 10 and a paper information management server 50 are connected to the local area network 1. Further, a medical image database (DB) 23, which is memory in a broad sense, is connected to the local area network 1. A medical document database (DB) 22, which is memory in a broad sense for storing electronic documents that are a source of document images formed on a sheet of chart paper 70, is connected to the paper information management server 50. Other medical documents such as a letter of introduction, a letter of consent or a medical certificate in addition to information described in a sheet of medical chart paper and information about an electronic chart are stored in this medical document DB 22. The paper information management server 50 has a function of associating paper information with electronic information as described later. Also, a printer 100 (described below) for outputting a sheet of chart paper (paper medical chart) 70 on which a document image prepared based on various electronic documents and a code image prepared based on code information are formed is connected to the local area network 1. The printer 100 forms a document image on a medium (a sheet of paper) using colored toner/colored ink of YMCK etc. by, for example, an electrophotography method or an ink-jet method. Also, the printer 100 forms a code image on the medium (the sheet of paper) using, for example, invisible toner to the sheet of chart paper 70 as described below.

Also, the doctor's terminal 3 is equipped with application software for accepting an input of an electronic pen 5. This electronic pen 5 has a writing part functioning as a normal pen, used to write characters or graphics on a sheet of paper by an operation similar to that of the normal pen. Also, the electronic pen 5 has a function of recognizing a code image printed with invisible toner in addition to this writing part. More specifically, the electronic pen has an infrared-light exposure function of applying infrared light in order to read a code image on a sheet of paper and an image input function of capturing a code image to which the infrared light is applied and inputting the captured code image. Further, the electronic pen 5 has a function of monitoring movement of the writing part and detecting that the tip end of the electronic pen 5 is pressed on the sheet of paper. Also, the electronic pen 5 has a control section for controlling the whole electronic action of the electronic pen 5.

When a user writes characters or graphics on the sheet of chart paper 70 with the electronic pen 5, the control section acquires a detection signal indicating that recording is made on the sheet with the pen from, for example, a writing pressure detection function. Upon detecting this detection signal, the control section instructs the infrared-light exposure function to apply the infrared light to the sheet. The infrared light, which is applied to the sheet of chart paper 70 by this infrared-light exposure function, is absorbed by an invisible image.

The image input function captures a code image to which this infrared light is applied. Then, the control section of the electronic pen 5 analyzes the image input from the image input function and acquires a code. With respect to the acquired code, the control section of the electronic pen 5 corrects a deviation between coordinates of the pen tip of the writing part and coordinates of the image captured by the image input function to calculate a locus of the pen tip. This calculated locus information is stored in memory built into the electronic pen 5. Thereafter, this locus information is sent to the doctor's terminal 3 via, for example, a USB, a wireless LAN, RS-232C or Bluetooth at predetermined timing. As described above, the electronic pen 5 is used in the sheet of chart paper 70 on which a code image prepared based on code information including information available to identify a medium is printed. Also, the electronic pen 5 can acquire a code image corresponding to an operation position on the sheet of chart paper 70 in conjunction with an user's operation on the sheet of chart paper 70 and user's writing onto this sheet of chart paper 70.

A backbone database (DB) 21 for storing information about a backbone system is connected to the backbone system server 10. Also, as the computerizing systems, an inspection system 41 for managing basic information about a patient and a prescription system 42 for managing prescription for medicines and inspection measures are connected to the backbone system server 10. Further, computerizing systems of a reservation system 43 for managing various reservations for inspection, treatment and reexamination and an accounting system 44 for managing information about a demand for medical fees are connected thereto. Management between the backbone system server 10 and the backbone DB 21 and between these and various systems (41 to 44) are performed through predetermined identification codes. Inspection information, prescription information, reservation information and accounting information are managed with, for example, an inspection ID, a prescription ID and a reservation ID. In this exemplary embodiment, these are linked (associated) by a medical chart ID described below.

Here, generally, information about a demand for examination fees is mainly managed in a backbone system in a medical institution. On the other hand, various medical images, inspection results and medical records used in actual medical treatment are handled in a system different from the backbone system, and are stored in a database while being identified by an inspection ID, a prescription ID and a reservation ID. In an example of the exemplary embodiment shown in FIG. 1, various systems (41 to 44) manage and store information about medical documents in the medical image DB 23. That is, various medical images, inspection results and medical records used in actual medical treatment are stored in the medical image DB 23 with being identified by an inspection ID, a prescription ID, a and reservation ID linked by a medical chart ID.

Incidentally, the front desk terminal 2, the doctor's terminal 3 and various terminals 4 shown in FIG. 1 use various hardware resources (not shown) as a personal computer (PC). Also, the paper information management server 50, the backbone system server 10, the inspection system 41, the prescription system 42, the reservation system 43 and the accounting system 44 are implemented by using various hardware resources (not shown) as a kind of computer. These hardware resources comprise a CPU (Central Processing Unit) which is computation means, and also comprise main memory connected to the CPU through, for example, an M/B (mother board) chip set and a CPU bus, and a video card connected to the CPU through, for example, an M/B chip set and an AGP (Accelerated Graphics Port) similarly. Further, they comprise, for example, a network interface, a magnetic disk device (HDD) connected to an M/B chip set through a PCI (Peripheral Component Interconnect) bus, a keyboard/mouse or various disk drives connected to an M/B chip set through a low-speed bus such as an ISA (Industry Standard Architecture) bus and a bridge circuit from this PCI bus. Furthermore, the electronic pen 5 comprises a CPU or memory such as various ROM or RAM, and implements various computation processing or communication processing, etc. using hardware resources.

Figure 2:
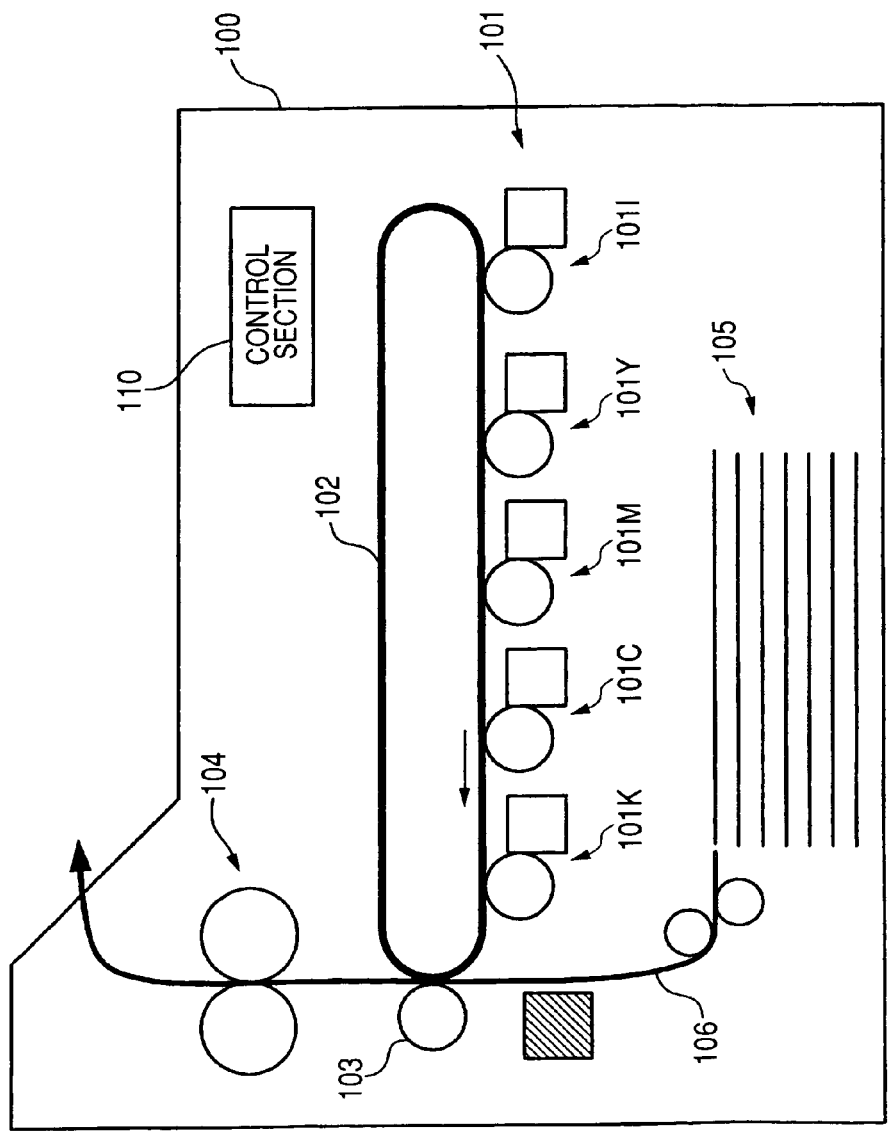
FIG. 2 is an explanatory diagram showing one exemplary embodiment of a printer.

FIG. 2 is an explanatory diagram showing one exemplary embodiment of the printer 100. The printer 100 simultaneously prints a document image, which is a visible image, and a code image, which is an invisible image, by means of, for example, an electrophotography method. For that purpose, the printer has five image formation units 101 (101I, 101Y, 101M, 101C, 101K) for forming toner images for invisible, yellow, magenta, cyan, black on photoconductor drums, and an intermediate transfer belt 102 to which these toner images are sequentially transferred in an example shown in FIG. 2. A code image is formed by this image formation unit 101I for invisible and document images are formed by the other image formation units 101Y, 101M, 101C, 101K. Also, the printer has a secondary transfer roll 103, a fixing device 104, a sheet tray 105, a transport path 106 and a control section 110. The secondary transfer roll 103 collectively transfers superimposed toner images onto a medium (a sheet of paper) being transported. The fixing device 104 fixes the toner images formed on the medium (the sheet of paper). Also, the sheet tray 105 supplies the medium (the sheet of paper) being transported. The transport path 106 transports the medium (the sheet of paper) supplied from the sheet tray 105. Further, the control section 110 performs various processing about printing of the document image and the code image while performing the whole control of the printer 100.

For example, when a patient passes an examination card at the front desk of a hospital, patient ID information stored in the examination card is read by a card reader (not shown) connected to the front desk terminal 2 and information about a patient's visit to a hospital is acquired. Then, based on the read information, for example, print instructions are output from the doctor's terminal 3 or the front desk terminal 2 disposed in the front desk. The print instructions are sent to the paper information management server 50. Then, a code image and a document image to be printed are sent from the paper information management server 50 to the printer 100. In this manner, the sheet of chart paper 70 used on the day is output from the printer 100 installed in, for example, a medical department for having an examination. As shown in FIG. 2, the printer 100 can form a visible image using toner of four colors of YMCK and form an invisible image using invisible toner to thereby print on a paper medium an image on which the visible image and the invisible image are superimposed. The invisible toner has characteristic of absorbing light having a wavelength of an infrared or ultraviolet region though the toner is transparent (or substantially transparent) when viewed with eyes. The invisible toner is machine-readable by applying infrared or ultraviolet light thereto.

Figure 3:
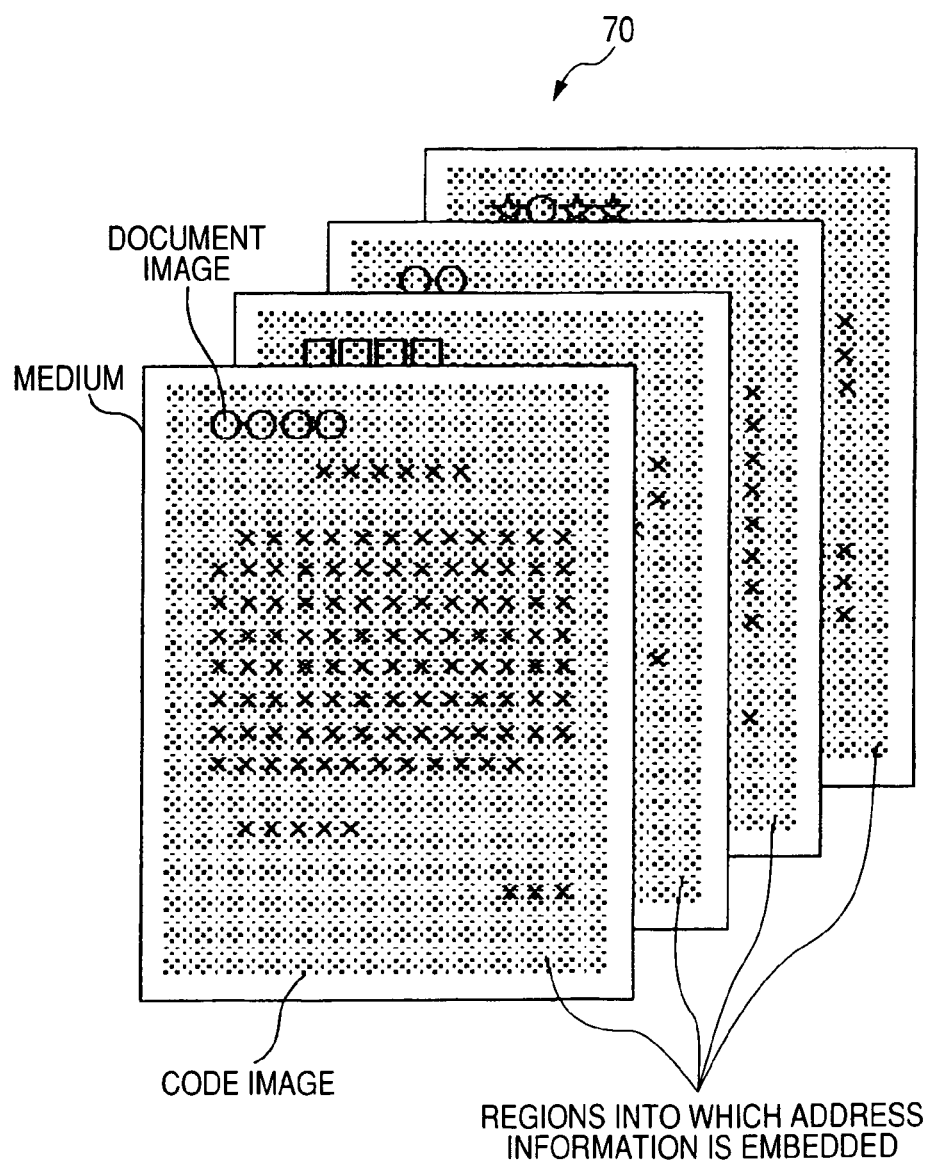
FIG. 3 is a diagram showing a structure of medical charts output by the printer.

FIG. 3 is a diagram showing a structure of the sheet of chart paper 70 output by the printer 100. As shown in FIG. 3, in the sheet of chart paper 70, the document image formed with the visible toner and the code image printed with invisible toner are formed on a surface of a medium (a sheet of paper). This code image includes address information (position information), identification information and other additional information. This address information is allocated to the entire surface of the medium according to a size of the printing medium. The code image in which the address information is encoded is formed on the entire surface of the medium. However, printing of the code image is not limited to the case of using an invisible color material. For example, the code image may also be formed with carbon black for absorbing a wavelength of an infrared region and the document image may be formed with color materials (these color materials normally have a small amount of absorption of a wavelength of an infrared region) of yellow, magenta and cyan.

As this code image, for example, a two-dimensional code pattern may be adopted. Exemplary examples of the two-dimensional code pattern include a combination of slashes "/" and back slashes "\," which is disclosed in U.S. patent application Ser. No. 11/250,401 and U.S. Patent Application filed on Mar. 10, 2006 with claim for foreign priority of Japanese Patent Application No. 2005-171885, which are incorporated by reference in its entirety. Then, as invisible toner used in printing of such a two-dimensional code pattern, for example, the toner in which the maximum absorptance in a visible light region (400 nm to 700 nm) is, for example, 7% or less and absorptance in a near-infrared region (800 nm to 1000 nm) is, for example, 30% or more may be used. Also, in order to improve a near-infrared light absorption capacity necessary for machine reading of an image, the toner whose average dispersion diameter is in the range of 100 nm to 600 nm is adopted as this invisible toner. Here, "visible" and "invisible" do not depend on whether or not recognition can be made with eyes. Distinction between "visible" and "invisible" is made based on a result as to whether or not an image formed on a printed medium can be recognized based on the presence or absence of color caused by absorption of a particular wavelength in a visible light region. Also, this two-dimensional code pattern includes a region in which a position code (code corresponding to address information) is stored and a region in which an identification code for uniquely specifying a print medium or an electronic document is stored. Also, the two-dimensional code pattern includes a region in which a code of additional information and a synchronous code are stored. Then, plural two-dimensional code patterns respectively having these contents are arranged on the entire surface (paper surface) of a medium according to a size of the medium printed. Also, each bit value is formed of plural minute line bit map shaving different rotational angles, and bit 0 and bit 1 are represented using, for example, a slash "/" and a backslash "\" having different inclinations from each other. For example, a slash pattern is constructed of a size of 8 by 8 pixels at 600 dpi, and a slash pattern (pattern 0) extending from bottom right to top left represents a bit value 0 and a slash pattern (pattern 1) extending from bottom left to top right represents a bit value 1. Therefore, 1 bit information (0 or 1) can be represented by a single slash pattern.

Figure 4B:
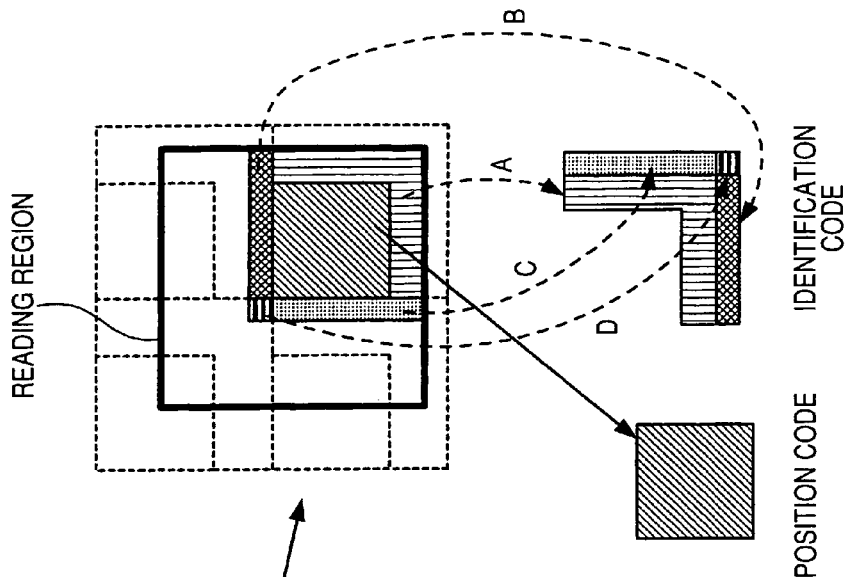
FIGS. 4A and 4B are diagrams to explain reading a code image formed on the medical chart as shown in FIG. 3 by means of an electronic pen.
Figure 4A:
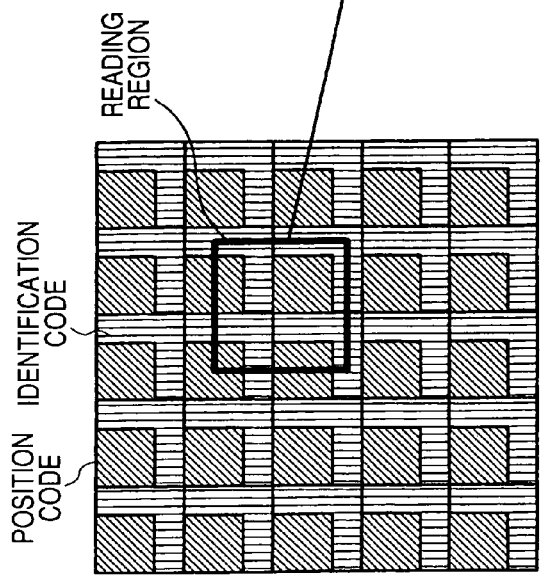

FIGS. 4A and 4B are diagrams to explain reading a code image formed on the sheet of chart paper 70 as shown in FIG. 3 by means of the electronic pen 5. As shown in FIG. 4A, the plural position codes (codes corresponding to address information) and the plural identification codes (codes corresponding to identification information) are respectively arranged two-dimensionally on the sheet of chart paper printed by the printer 100. For the convenience of description, a synchronous code is not shown in FIG. 4A. A position code region stores, for example, position information of 36 bits in total. Of the 36 bits, for example, 18 bits may be used in encoding of X coordinates and the remaining 18 bits may be used in encoding of Y coordinates. If all of 18 bits are used in position encoding, positions of 218 ways (about 260,000 ways) can be encoded. In the case of forming a code image using the slash patterns of the slash "/" and the backslash "\" described above, it is assumed that each of the slash patterns is formed of, for example, 8 pixels by 8 pixels (at 600 dpi). Since one dot at 600 dpi is 0.0423 mm, a size of a single two-dimensional code (in case that it is formed of 9 bits by 9 bits including a synchronous code) including a single position code and a single identification code is equal to about 3 mm long and about 3 mm wide (8 pixels by 9 bits by 0.0423 mm). FIG. 4A shows an example where 25 two-dimensional codes each having about 3 mm long and about 3 mm wide in size are arranged. If positions of 260,000 ways are encoded at 3-mm intervals, a length of about 786 m can be encoded. Thus, all the 18 bits may be used in encoding of the positions. Also, when a detection error of the slash pattern occurs, a redundancy bit for error detection or error correction may be included. Also, for example, the identification code is arranged in rectangular regions of 2 bits by 8 bits and 2 bits by 6 bits. Identification information of 28 bits in total can be stored. If 28 bits are used as identification information, identification information of about 270,000,000 ways ($2^{28}$ ways) can be represented. The identification code can also include a redundancy bit for error detection or error correction in 28 bits in a manner similar to the position code.

Then, as described above, position information different by an arranged place is stored in each of the plural position codes. The same identification information regardless of an arranged place is stored in the plural identification codes. Now, it is assumed that a reading region (minute range) of an invisible image read by the electronic pen 5 is shown by a thick line of FIG. 4A. An enlarged diagram of the vicinity of this reading region is shown in FIG. 4B. Since the position code contains information different by a position on the image, the position code cannot be detected unless one or more position codes are included in the read image. However, since the identification code contains the same identification information regardless of a position on the image, a position code can be reconstructed from fragmentary information. In an example shown in FIG. 4B, four partial codes (A, B, C, D) in the minute range of the reading region is combined to enable to reconstruct a single identification code.

FIG. 5 is a diagram showing an example of a medical chart form formed on the sheet of chart paper 70. Layout information such as ruled lines of the medical chart form is printed on the sheet of chart paper 70 with the visible toner by means of the printer 100 as described above. Also, concurrently with this, a code image—in which identification information (medical chart ID) capable of uniquely specifying a medical chart one by one and address information capable of specifying a position (coordinate) on the sheet of chart paper 70 are encoded—is printed on the entire surface of the sheet of chart paper 70 with the invisible toner. The code image is read by applying infrared or ultraviolet light to the code image. Also, the medical chart ID information and position information can be read by decoding the read code image. Although the code image is printed on almost the entire surface of the sheet of paper, since the code image is printed with the invisible toner, information such as form layout printed with the visible toner can be clearly read with eyes.

As shown in this FIG. 5, the medical chart form of the sheet of chart paper 70 is provided with patient basic information 71 such as a patient name, the date of birth, a patient facial photograph, an anamnesis and allergy information and a free handwriting entry field 72 corresponding to a medical chart form. Also, in addition to these areas, the medical chart form is provided with an entry type selection field 73, a past history reference instruction field 74 and a system linkage function field 75. Further, a watermark image 76 using the invisible toner is formed thereon.

As described above, the identification information (medical chart ID) and the position information on paper are printed on the entire surface of the sheet of chart paper 70 as the code image. When a handwriting input is done on the sheet of chart paper 70 using the electronic pen 5 capable of reading the code image, the electronic pen 5 simultaneously detects the medical chart ID and the position information. As a result, information as to which position of the sheet of chart paper 70 handwriting is performed can be acquired as electronic information. Further, time information as to "what time handwriting is made" can be acquired by using time information held by the electronic pen 5 or the terminal device side (doctor's terminal 3) for acquiring information from the electronic pen 5.

A doctor enters a medical record in the free handwriting entry field 72 formed on the medical chart form of the sheet of chart paper 70 based on examination of a patient, using the electronic pen 5. The electronic pen 5 is provided with a reading device (for example, an infrared-light exposure function and an image input function) for reading a code image printed with the invisible toner using infrared light as described above. Therefore, by decoding the read code image, a movement locus of the electronic pen 5 on the sheet of chart paper 70 and a medical chart ID are detected and it can be recognized what handwriting is entered in any medical chart or which position on the sheet of chart paper 70 the electronic pen 5 points.

The contents entered in the free handwriting entry field 72 of this sheet of chart paper 70 may include the contents corresponding to S, O, A, P as shown in the entry type selection field 73 of FIG. 5. For example, a major complaint (S: subjective) is specified and a subjective symptom of a patient is entered. Also, an objective finding (O: objective) is specified and an inspection finding and/or an examination finding by a doctor is entered. Further, diagnosis (A: assessment) is specified and diagnosis by a doctor, differential diagnosis, evidence and selection of a treatment method and assessment on treatment are entered. Furthermore, a plan (P: plan) is specified and a treatment plan is entered.

In the case of computerizing the contents written on the sheet of chart paper 70 by the electronic pen 5, all the information written in the free form can also be sent and stored in a database (medical document DB 22, etc.) as a single piece of electronic data. However, for example, by storing entry items with being classified into the entry items as shown in FIG. 5, it would be helpful for making secondary use of medical chart entry data, for example, retrieval of diagnosis (A) data with respect to items of the same major complaint (S) or retrieval of diagnosis (A) data with respect to the same objective finding (O). In the medical chart form shown in FIG. 5, the entry type selection field 73 is used for assigning classification to the entry items thus. When a doctor describes information about a major complaint (S), a tag of S is assigned to data in which the described contents are computerized by checking a check box of S before or after the description. As a result, the data can be stored in a database in a form of assigning attribute information about classification to the entry items.

Next, functions of the medical document 22 and the paper information management server 50 in the medical information system shown in FIG. 1 will be described.

FIG. 6 is a block diagram showing a function of the medical document 22 and the paper information management server 50. The paper information management server 50 has various functions of associating paper information with electronic information. As the functions, the server 50 has a print instruction input section 51 and a patient information input section 52. The print instruction input section 51 is input a print instruction of the sheet of chart paper 70 given from the front desk terminal 2 or the doctor's terminal 3. The patient information input section 52 is input patient information such as a medical chart ID and information to be printed on the patient basic information 71 shown in FIG. 5, in accordance with the print instruction by the print instruction input section 51. When there is the fact that a patient was examined in the past, for example, reexamination, an ID (described below) having an attribute for handwritten data classified into types of S, O, A, P is also input by the patient information input section 52.

Also, the paper information management server 50 further has a document image generation section 53, a code image generation section 54, a document image output section 55, a code image output section 56, a handwritten information recognition section 57, a selection field specification recognition section 58, a medical chart ID specifying section 59, a function selection specifying section 60, a medical chart ID output section 61 and a functional order output section 62. The document image generation section 53 generates a document image. The code image generation section 54 generates a code image. The document image output section 55 outputs the generated document image to the printer 100. The code image output section 56 outputs the generated code image to the printer 100, similarly. The handwritten information recognition section 57 recognizes handwritten information based on the pen locus of the electronic pen 5. The selection field specification recognition section 58 recognizes the pen locus of the electronic pen 5 with respect to a function selection field provided on the sheet of chart paper 70 as shown in FIG. 5. The medical chart ID specifying section 59 specifies a medical chart ID. The function selection specifying section 60 specifies a function selection made by a user (doctor) using the electronic pen 5. The medical chart ID output section 61 outputs the medical chart ID specified by the medical chart ID specifying section 59 to the backbone system server 10. The functional order output section 62 outputs a functional order specified by the function selection specifying section 60 to the backbone system server 10.

On the other hand, the medical document DB 22 may be classified into a medical chart form DB 22a, a code information DB 22b, a handwritten information DB 22c and an other medical document DB 22d. The medical chart form DB 22a stores the medical chart form as shown in FIG. 5 generated in the easiest-to-use format for each medical department such as the department of internal medicine, the department of surgery, the department of pediatrics, the department of dermatology, the department of obstetrics and gynecology and the department of orthopedics. The code information DB 22b stores the patterns such as slash patterns of a slash "/" and a backslash "\" having different inclinations from each other as described above. Also, the code information DB 22b stores various pieces of information necessary to generate code information such as additional information, address information (position information) and information used to arrange these patterns two-dimensionally. The handwritten information DB 22c stores handwritten data to which an ID having an attribute is allocated in accordance with a type of, for example, S, O, A, P. The handwritten data stored herein is data obtained by acquiring the movement locus of the electronic pen 5 by means of the code image printed with invisible toner. The other medical document DB 22d stores various other medical documents such as a letter of introduction, a letter of consent or a medical certificate.

FIG. 7 is a flowchart showing image generation processing performed by the paper information management server 50 shown in FIG. 6. For example, when the medical chart as shown in FIG. 5 is created, the document image generation section 53 first analyzes a print instruction input from the print instruction input section 51 (step 101). Then, the document image generation section 53 reads a particular medical chart form dedicated to, for example, internal medicine or surgery from the medical chart form DB 22a, based on the contents of the analyzed print instruction (step 102). Also, the document image generation section 53 acquires patient information from the patient information input section 52 in order to generate, for example, the patient basic information 71 as shown in FIG. 5 (step 103). Here, the patient information input section 52 analyzes input patient information, and decides whether or not there is past medical history (step 104). When there is the medical history, particular handwritten information is read from the handwritten information DB 22c using, for example, an ID of the input handwritten data and the document image generation section 53 acquires the handwritten information (step 105). When the patient information input section 52 decides that there is no medical history in step 104, the flowchart proceeds to step 106 as it is. The document image generation section 53 generates the document image based on the medical chart form and the handwritten information, which are read out (step 106).

On the other hand, the code image generation section 54 reads out the slash patterns (code patterns) of, for example, the slash "/" and the backslash "\", which have different inclinations from each other and are stored in the code information DB 22b, which is memory (step 107). Also, the code image generation section 54 reads the position information from the code information DB 22b (step 108). Further, the code image generation section 54 acquires the medical chart ID from the patient information input section 52 (step 109). Then, the code image generation section 54 generates a two-dimensional code image formed of the slash patterns using the acquired medical chart ID and the read position information (step 110). The document image generated by the document image generation section 53 and the code image generated by the code image generation section 54 are output to the printer 100 through the document image output section 55 and the code image output section 56, respectively (step 111). Then, the image generation processing is ended. The printer 100 prints the acquired document image on the medium (the sheet of paper) using the visible toner of Y, M, C, K. On the other hand, the printer 100 prints the acquired code image on the medium (the sheet of paper) using the invisible toner. As a result, the sheet of chart paper 70 as described with reference to FIGS. 3 to 5 can be printed.

Identification information included in the code information used as a source of the code image is information available to uniquely specify a medical chart one by one. In the example shown in FIG. 7, the medical chart ID acquired in step 109 is used as the identification information. Identification information of the printer 100 including information of a counter value of printing or the identification information of the printer 100 including time information of printing may be used as the information, which can be used to uniquely specify the sheet of chart paper one by one. In the case of using such identification information, it is preferable to generate a code and generate an image by means of a code image generation function provided for the printer 100 instead of the code image generation section 54 of the paper information management server 50.

Next, a structure of the backbone DB 21 shown in FIG. 1 will be described.

FIG. 8 is a diagram showing data structures of a medical chart information database (DB) (FIG. 8A), a patient information database (DB) (FIG. 8B) and an inspection information database (DB) (FIG. 8C) in the backbone DB 21. The backbone DB 21 shown in FIG. 1 is constructed by plural databases on a function basis, for example, prescription information database (DB), reservation information database (DB) and accounting information database (DB) in addition to the databases shown in FIGS. 8A to 8C. These databases are used in the case of executing computerizing systems such as the inspection system 41, the prescription system 42, the reservation system 43 and the accounting system 44 connected to the backbone system server 10.

As shown in FIG. 8A, the medical chart information DB stores a medical chart ID 31 assigned to every medium of a paper medical chart and a patient ID 32 corresponding to the medical chart ID 31. For example, when a patient is specified and the sheet of chart paper 70 is printed out, predetermined data corresponding to the medical chart ID 31 is stored into the medical chart information DB. Also, when a check box (entry type selection field 73 shown in FIG. 5) is checked in S, O, A, P types of handwritten information, an ID having an attribute is allocated to handwritten data entered subsequently and the ID of handwritten information is stored in the medical chart information DB. FIG. 8A shows an ID (S_Box_1) 33 of the handwritten information about a major complaint (S) of the stored S, O, A, P types as a representative example of S, O, A, P types. Similarly, the medical chart information DB stores an ID (O_***_*) of handwritten information about the same objective finding (O), an ID (A_***_*) of handwritten information about diagnosis (A) and an ID (P_***_*) of handwritten information about a plan (P).

Also, when the system linkage function field 75 of the sheet of chart paper 70 shown in FIG. 5 is checked, an inspection ID 34 is acquired and an inspection image data ID and an inspection content are associated and are stored. When the inspection content reference field on a paper medical chart is specified using the electronic pen 5 after the inspection, information about the corresponding inspection ID can be seen.

As shown in FIG. 8B, various patient information is associated with a patient ID 36 corresponding to the patient ID 32 of the medical chart information DB shown in FIG. 8A and is stored in the patient information DB. The contents of the patient information DB shown in this FIG. 8B are reflected on the sheet of chart paper 70 as the patient basic information 71 shown in FIG. 5.

Also, as shown in FIG. 8C, various inspection information is associated with an inspection ID 37 corresponding to the inspection ID 34 shown in FIG. 8A and is stored in the inspection information DB. In this inspection information DB, for example, an inspection image ID 38, which is identification information about an inspection image, is stored. In the medical image DB 23 shown in FIG. 1, for example, various images associated with this inspection image ID 38 are stored.

Each information is similarly stored in various databases of prescription, treatment and reservation. According to such a configuration, for example, a link between inspection information and an inspection order on the paper sheet of chart paper 70 can be performed easily and a seamless linkage between an ordering system and a handwriting action on the paper sheet of chart paper 70 can be performed.

Next, a linkage between a computerizing system (for example, an ordering system) of computerized inspection, prescription, treatment, examination reservation, etc. and the paper sheet of chart paper 70 to which the present embodiment is applied will be described in further detail.

Description will be made herein on a linkage to the inspection system 41 as an example. It is assumed that a doctor examines a patient and, for example, a roentgen inspection is required. In this case, a doctor enters a check in an IN check box of an area written as "inspection" printed in the system linkage function field 75 on the medical chart form of the sheet of chart paper 70 shown in FIG. 5 by the electronic pen 5. The electronic pen 5 reads code information printed on the sheet of chart paper 70 with the invisible toner, and sends the code information to the paper information management server 50. In the paper information management server 50, the selection field specification recognition section 58 shown in FIG. 6 acquires the code information and the medical chart ID specifying section 59 specifies a medical chart ID. Also, the function selection specifying section 60 recognized a specified function based on the recognized position information. Then, the paper information management server 50 outputs the contents of the recognized medical chart ID and the contents of a functional order to the backbone system server 10 through the medical chart ID output section 61 and the functional order output section 62.

Alternatively, the electronic pen 5 may recognize all the medical chart ID and the position information, and directly send to the backbone system server 10 information as to which position of the medical chart of which patient a check mark is entered.

The backbone system server 10 on the computerizing system side receives the information from the paper information management server 50 or the electronic pen 5, and decides which ordering system an input regarding which patient is requested to. Then, for example, the inspection system 41 displays a menu of the requested ordering system on a display of the doctor's terminal 3 installed in a desk of a doctor of an examination room. The doctor inputs the contents of an inspection to be made from a menu screen displayed on the display of the doctor's terminal 3. The inspection system 41 receiving the input from the doctor's terminal 3 sends patient information and information about the ordered contents to an ordered inspection department (for example, a roentgen department) in accordance with the input order contents. Also, inspection guidance in which reservation time and a place for making an inspection of roentgen are printed is output to the printer 100 installed in, for example, an examination room and is passed to a patient.

Also at this time, when a check is made in an inspection IN check box of the system linkage function field 75 shown in FIG. 5, an individual inspection ID is acquired. The backbone system server 10 associates the acquired inspection ID with the backbone DB 21 and stores patient identification information (patient ID 32) and order information about the contents of inspection. The patient moving from the examination room to the inspection department undergoes the order inspection in the inspection department. Various information such as blood inspection data, waveform data of an electrocardiogram and a roentgen image, which are inspection results, are stored in databases such as the backbone DB 21 or the medical image DB 23.

A method in which only an ID is issued as the inspection ID 34 and data is stored in a form of associating the inspection ID 34 with corresponding patient data, order data and inspection result data may be adopted. Also, as shown in FIG. 8C, a method for reserving a data region along with the inspection ID 34 and storing data corresponding to the reserved data region may be adopted.

The patient who has undergone the inspection again enters the examination room, and undergoes diagnosis by the doctor based on the inspection results. When the doctor refers to the inspection results, a check mark is entered in a View check box (under an IN check box checked at the time of ordering) of an area written as "inspection" of the system linkage function field 75 on a medical chart form of the sheet of chart paper 70 by the electronic pen 5. The electronic pen 5 recognizes code information printed on the sheet of chart paper 70 with the invisible toner. Then, the electronic pen 5 recognizes the medical chart ID 31 and position information, and sends information as to which position of a medical chart of which patient a check mark is entered to the backbone system server 10. Or, the paper information management server 50 receives code information recognized by the electronic pen 5, and specifies the medical chart ID 31 and a function, and sends information as to which position of a medical chart of which patient a check mark is entered to the backbone system server 10.

The inspection system 41 on the computerizing system side receives the information, and decides which inspection result regarding which patient is required to reference to. Then, the requested inspection results (for example, a roentgen image, waveform data or numerical data) are displayed on a display of the doctor's terminal 3 installed in a desk of the doctor of the examination room. The doctor refers to the inspection results displayed on the display and makes diagnosis.

According to this exemplary embodiment, the computerizing system can be called up from the sheet of chart paper 70. Further, reference work can be implemented by entry to the sheet of chart paper 70 by means of the electronic pen 5. Also, the display of the doctor's terminal 3 may be of, for example, a touch panel type.

Also, when a patient has a reexamination, a check mark may be entered in a View check box of the past history reference instruction field 74 on a medical chart form of the sheet of chart paper 70 by the electronic pen 5. In a manner similar to the recognition described above, by the electronic pen 5 or the paper information management server 50, a medical chart ID and the selected contents are specified and are sent to the backbone system 10. As a result, on the side of the computerizing systems (41 to 44) connected to the backbone system server 10, prescription information, inspection information and medical chart information (may be a handwritten image or text processed by OCR) at the time of the past examination can be specified and displayed on the display of the doctor's terminal 3. As a result of this, a doctor can refer to the past acquired medical chart information etc. and use the medical chart information etc. in the next medical treatment. Incidentally, in selection of the past reference histories, a form on the sheet of chart paper 70 may be selected every item and also, it can be constructed so as to make selection on the computerizing system.

What is claimed is:

1. An electronic document management system comprising:
    an acquisition unit,
    a medium comprising a document image, and
    a plurality of code images two-dimensionally arranged, each of the code images comprising position information and medium identification information uniquely identifying the medium as a particular medium type and a specific instance of the medium type,
    wherein the medium identification information includes associated attribute information and the electronic document management system is configured to allow a user to dynamically retrieve medium identification information of associated medium instances by forming associations between medium instances that share a common attribute from the database, where the attribute information relates to specific attributes for a person and can identify the attributes related to the person, and where the attribute information can be designated by the user when storing each of the medium instances, and
    the acquisition unit acquires a code image corresponding to an operation position on the medium in conjunction with a user's operation with respect to the medium, wherein the acquisition unit is capable of reconstructing the medium identification information from fragmentary information included in a reading region;
    a specifying unit that specifies the medium identification information included in the code image acquired by the acquisition unit;
    an application execution unit that executes an application in response to the user's operation, the execution occurring at nearly the same time as the user's operation; and
    a database that stores personal information associated with the medium identification information specified by the specifying unit.

2. The system according to claim 1, wherein:
    predetermined position information included in the code images two-dimensionally arranged on the medium is associated with a predetermined computerizing system, and
    the system executes the predetermined computerizing system based on the predetermined position information included in the code image acquired by the acquisition unit.

3. The system according to claim 1, wherein:
    the medium is a sheet of chart paper used in medical practice, and
    the medium identification information is identification information used for uniquely identifying the sheet of chart paper as a particular chart type and a specific instance of the chart type.

4. The system according to claim 1, wherein the code images are printed with an invisible color material having characteristic that absorbs a predetermined wavelength of an infrared region more than a wavelength of a visible light region.

5. The system according to claim 1, wherein the code images cover a substantial portion of a surface of the medium.

6. The electronic document management system according to claim 1, wherein each of the code images further comprises additional information including synchronous information or time of printing.

7. A medical information system comprising:
    an electronic pen used for a sheet of chart paper on which a plurality of code images are printed, each of the code images formed on a basis of medium identification information comprising information to uniquely identify the sheet of chart paper as a particular chart type and a specific instance of the chart type, the electronic pen used to write onto the sheet of chart paper, the electronic pen acquires a code image corresponding to an operation position on the sheet of chart paper in conjunction with a user's operation with respect to the sheet of chart paper, wherein the medium identification information is capable of being reconstructed from fragmentary information included in a reading region read by the electronic pen, and
    wherein the medium identification information includes associated attribute information and the electronic document management system is configured to allow a user to dynamically retrieve medium identification information of associated chart instances by forming associations between chart instances that share a common attribute from the database, where the attribute information relates to specific attributes for a person and can identify the attributes related to the person, and where the attribute information can be designated by the user when storing each of the chart instances, and an application execution unit that executes an application in response to the user's operation, the execution occurring at nearly the same time as the user's operation; and a database that stores personal information while associating the personal information with the information to uniquely identify the sheet of chart paper as a particular chart type and a specific instance of the chart type, wherein the system accesses predetermined personal information stored in the database with using information to uniquely identify the sheet of chart paper as a particular chart type and a specific instance of the chart type included in the code image acquired in conjunction with the user's operation of the electronic pen.

8. The system according to claim 7, wherein:
each code image comprises position information on the sheet of chart paper,
the electronic pen acquires the position information in conjunction with a user's writing operation to acquire a locus of the user's writing operation, and
the database stores information about the locus acquired by the electronic pen with the information about the locus being associated with the information available to identify the sheet of chart paper.

9. The system according to claim 7, wherein:
each of the code images comprises position information on the sheet of chart paper,
the electronic pen acquires the position information on the sheet of chart paper in conjunction with the user's operation of the electronic pen to specify the user's operation position, and
the system executes a predetermined electronic medical support system associated on a basis of the operation position specified by the electronic pen and the electronic medical support system.

10. The system according to claim 7, wherein the electronic medical support system processes at least one of an order for inspection, an order for prescription and an order for reservation.

11. The system according to claim 7, wherein when the sheet of chart paper is printed by means of a printer, the database stores chart information while associating the chart information with the information to uniquely identify the sheet of chart paper as a particular chart type and a specific instance of the chart type included in the code information, which is a source of code image on the sheet of chart paper.

12. The system according to claim 7, wherein the code images cover a substantial portion of a surface of the sheet of chart paper.

13. The medical information system according to claim 7, wherein each of the code images further comprises additional information including synchronous information or time of printing.

14. A sheet of chart paper used in medical practice, the sheet of chart paper printed during the medical practice, the sheet of chart paper comprising:
a document image that comprises:
a predetermined chart form, and
patient information,
the document image printed with a color material, which is recognizable with human eyes; and
a plurality of code images printed on the sheet of chart paper with a color material having characteristic that a wavelength of a particular infrared region is absorbed more than a wavelength of a visible light region, each of the code images comprising:
position information that specifies a position on the sheet; and
identification information uniquely identifying the chart as a particular chart type and a specific instance of the chart type;
the position information and the identification information being in a fine region, which can be readable by an electronic pen that captures a user's operation with respect to the sheet of chart paper, wherein the identification information is capable of being reconstructed from fragmentary information in the fine region, and
wherein the identification information includes associated attribute information and the electronic document management system is configured to allow a user to dynamically retrieve identification information of associated chart instances by forming associations between chart instances that share a common attribute from the database, where the attribute information relates to specific attributes for a person and can identify the attributes related to the person, and where the attribute information can be designated by the user when storing each of the chart instances.

15. The sheet of chart paper according to claim 14, wherein the identification information included in the code image is used when the patient information is stored in a database.

16. The sheet of chart paper according to claim 14, wherein the document image comprises handwritten information entered in a medical chart by a doctor.

17. The sheet of chart paper according to claim 14, wherein the code images cover a substantial portion of a surface of the sheet of chart paper.

18. The sheet of chart paper according to claim 14, wherein each of the code images further comprises additional information including synchronous information or time of printing.

19. An electronic document management system comprising:
an acquisition unit,
a medium comprising a document image, and
a plurality of code images two-dimensionally arranged, each of the code images comprising position information and medium identification information uniquely identifying the medium as a particular medium type and a specific instance of the medium type,
wherein the medium identification information includes associated attribute information and the electronic document management system is configured to allow a user to dynamically retrieve medium identification information of associated medium instances by forming associations between medium instances that share a common attribute from the database, and where the attribute information can be designated by the user when storing each of the medium instances, and
the acquisition unit acquires a code image corresponding to an operation position on the medium in conjunction with a user's operation with respect to the medium, wherein the acquisition unit is capable of reconstructing the medium identification information from fragmentary information included in a reading region;

a specifying unit that specifies the medium identification information included in the code image acquired by the acquisition unit;
an application execution unit that executes an application in response to the user's operation, the execution occurring at nearly the same time as the user's operation; and
a database that stores personal information associated with the medium identification information specified by the specifying unit, wherein the medium is a sheet of chart paper used in medical practice, and the medium identification information is identification information used for uniquely identifying the sheet of chart paper as a particular chart type and a specific instance of the chart type.

* * * * *